United States Patent
Song et al.

(10) Patent No.: US 11,946,043 B2
(45) Date of Patent: Apr. 2, 2024

(54) SELECTIVE LABELING OF 5-METHYLCYTOSINE IN CIRCULATING CELL-FREE DNA

(71) Applicant: Ludwig Institute for Cancer Research Ltd, Zurich (CH)

(72) Inventors: Chunxiao Song, Oxford (GB); Paulina Siejka, Oxford (GB)

(73) Assignee: Ludwig Institute for Cancer Research Ltd, Zurich (CH)

( * ) Notice: Subject to any disclaimer, the term of this patent is extended or adjusted under 35 U.S.C. 154(b) by 0 days.

(21) Appl. No.: 16/645,739

(22) PCT Filed: Sep. 11, 2018

(86) PCT No.: PCT/US2018/050465
§ 371 (c)(1),
(2) Date: Mar. 9, 2020

(87) PCT Pub. No.: WO2019/051484
PCT Pub. Date: Mar. 14, 2019

(65) Prior Publication Data
US 2020/0224190 A1 Jul. 16, 2020

Related U.S. Application Data

(60) Provisional application No. 62/556,718, filed on Sep. 11, 2017.

(51) Int. Cl.
*C12N 15/10* (2006.01)
*C12Q 1/6874* (2018.01)

(52) U.S. Cl.
CPC ....... *C12N 15/1065* (2013.01); *C12Q 1/6874* (2013.01)

(58) Field of Classification Search
CPC ... C12Q 1/6806; C12N 15/1093; C12N 15/10
See application file for complete search history.

(56) References Cited

U.S. PATENT DOCUMENTS

| | | | |
|---|---|---|---|
| 2014/0322707 A1* | 10/2014 | He | C12Q 1/6827 435/6.11 |
| 2015/0031552 A1 | 1/2015 | Gao et al. | |
| 2015/0218530 A1* | 8/2015 | Zheng | C12Q 1/6827 435/6.11 |
| 2017/0253924 A1 | 9/2017 | Lu et al. | |
| 2017/0298422 A1* | 10/2017 | Song | C12Q 1/6834 |

FOREIGN PATENT DOCUMENTS

| | | | |
|---|---|---|---|
| WO | 2012/138973 A2 | 10/2012 | |
| WO | 2015/027135 A1 | 2/2015 | |
| WO | WO-2015021282 A1 * | 2/2015 | ........... C12Q 1/6806 |
| WO | 2015/031552 A1 | 3/2015 | |
| WO | 2016/164363 A1 | 10/2016 | |
| WO | 2017/083562 A1 | 5/2017 | |

OTHER PUBLICATIONS

Song et al. (Nature biotechnology 29.1 (2011): 68-72) (Year: 2011).*
Yu et al. (Nature protocols 7.12 (2012): 2159). (Year: 2012).*
Hashimoto et al. ("Structure of a Naegleria Tet-like dioxygenase in complex with 5-methylcytosine DNA." Nature 506.7488 (2014):391-395.) (Year: 2014).*
Song et al. "Selective Chemical Labeling Reveals the Genome-Wide Distribution of 5-Hydroxymethylcytosine", Nat Biotechnol. 2011, vol. 1, pp. 1-11.
Miral Dizdaroglu et al., "Substrate specificity of the *Escherichia coli* endonuclease III: Excision of thymine- and cytosine-derived lesions in DNA produced by radiation-generated free radicals", Biochemistry, vol. 32, No. 45, 1993, pp. 12105-12111.
D. Jiang et al., "Characterization of *Escherichia coli* Endonuclease VIII", Journal of Biological Chemistry, vol. 272, No. 51, 1997, pp. 32230-32239.
Yibin Liu et al., "Bisulfite-free direct detection of 5-methylcytosine and 5-hydroxymethylcytosine at base resolution", Nature Biotechnology, Gale Group Inc., vol. 37, No. 4, 2019, pp. 424-429.
Hashimoto, Hideharu et al.: "Structure of a Naegleria Tet-like dioxygenase in complex with 5-methylcytosine DNA", Nature, vol. 506, No. 7488, Dec. 25, 2013 (Dec. 25, 2013), pp. 391-395.
Plongthongkum, Nongluk et al.: "Advances in the profiling of DNA modifications: cytosine methylation and beyond", Nature Reviews Genetics, vol. 15, No. 10, Aug. 27, 2014 (Aug. 27, 2014), pp. 647-661.
European Search Report dated Apr. 26, 2021, for related European Application No. 18853097.6, 8 pages.

* cited by examiner

*Primary Examiner* — Sahana S Kaup
(74) *Attorney, Agent, or Firm* — Fox Rothschild LLP

(57) ABSTRACT

The present disclosure provides methods for selectively tagging 5-methylcytosine in a DNA sample and using this approach for genome-wide profiling of 5-methylcytosine in a low input DNA sample such as circulating cell-free DNA.

25 Claims, 8 Drawing Sheets
Specification includes a Sequence Listing.

SELECTIVE LABELING OF 5-METHYLCYTOSINE IN CIRCULATING CELL-FREE DNA

FIELD OF THE INVENTION

This disclosure provides methods for selectively tagging 5-methylcytosine in a DNA sample and using this approach for genome-wide profiling of 5-methylcytosine in a DNA sample such as circulating cell-free DNA.

BACKGROUND

DNA modifications in the form of 5-methylcytosine (5mC) and 5-hydroxymethylcytosine (5hmC) represent the two major epigenetic marks found in the mammalian genome and they impact a broad range of biological processes from gene regulation to normal development. They represent distinct and antagonistic epigenetic features, with 5mC marking repressed genes and closed chromatin state, and 5hmC marking expressed genes and open chromatin state. Epigenetic information, including 5mC and 5hmC, is tissue and cancer-specific; and aberrant 5mC and 5hmC patterns are hallmarks of cancer.

Circulating cell-free DNA (cfDNA) is DNA found in blood, but originated from different tissues. cfDNA has been utilized for noninvasive prenatal tests, organ transplant diagnostics, and cancer detection.

Traditional cell-free methylated DNA sequencing methods utilize bisulfite sequencing, a harsh chemical treatment, which, due to extensive DNA degradation, requires relatively large amounts of DNA material, limiting its application. Bisulfite sequencing also cannot distinguish 5mC and 5hmC; therefore the repressive 5mC and activating 5hmC signals cannot be decoupled using bisulfite sequencing.

A selective chemical labeling-based, low-input whole-genome 5hmC sequencing method was previously developed that allows enrichment and sequencing of 5hmC in cfDNA, and demonstrated that cell-free 5hmC signatures can identify the tissue-of-origin in several cancer types. However, no method to date can sequence 5mC separately from cfDNA. The present invention provides a new low-input 5mC sequencing method suitable for cfDNA based on selective chemical labeling.

SUMMARY OF THE INVENTION

In one aspect, the invention provides a method for creating a library of 5-methylcytosine (5mC) containing DNA from a low input DNA sample comprising the steps of:
(a) obtaining a low input DNA sample;
(b) adding a blocking group to the endogenous 5-hydroxymethylcytosine (5hmC) in the DNA sample;
(c) converting the 5mC in the DNA sample to 5hmC;
(d) adding a linking group to the 5hmC from step (c);
(e) ligating DNA adapters to the DNA sample;
(f) adding an affinity tag to the linking group from step (d);
(g) enriching for the affinity tagged DNA from step (f) by affinity purification; and
(h) amplifying the enriched DNA from step (g).

In aspects, the invention involves a method for selective tagging of 5-methylcytosine (5mC) in a DNA sample comprising the steps of:
(a) adding a blocking group to the endogenous 5-hydroxymethylcytosine (5hmC) in the DNA sample;
(b) converting the 5mC in the DNA sample to 5hmC;
(c) adding a linking group to the 5hmC from step (b); and
(d) adding a tagging group (for example an affinity tag) to the linking group.

In embodiments of the invention, the DNA sample contains about 1 ng to about 10 ng of DNA, about 1 ng to about 5 ng of DNA, less than 10 ng of DNA, less than about 5 ng of DNA, or less that about 2 ng of DNA. In embodiments of the invention, the DNA sample comprises circulating cell-free DNA (cfDNA).

In embodiments of the invention, the blocking group is a glucose moiety. The glucose blocking group can be added to the endogenous 5hmC by contacting the DNA sample with uridine diphosphate (UDP)-glucose in the presence of β-glycosyltransferase ((βGT).

In embodiments of the invention, the step of converting the 5mC in the DNA sample to 5hmC comprises contacting the DNA sample with a ten eleven translocation (TET) enzyme. In embodiments of the invention, the TET enzyme is TET1. In preferred embodiments, the TET1 enzyme is *Naegleria gruberi* TET1 (NgTET1). In embodiments of the invention, the TET enzyme concentration is less than 3 µM, less than 2 µM, or less than 1 µM. In embodiments, the TET1 enzyme concentration is between about 0.5 µM and about 1 µM, for example about 0.75 µM.

In embodiments of the invention, the linking group is a modified glucose moiety, and the step of adding a linking group to the 5hmC generated from the endogenous 5mC comprises providing UDP linked to the modified glucose in the presence of βGT.

In embodiments of the invention, the steps of converting the 5mC in the DNA sample to 5hmC and adding a linking group to the 5hmC are performed as a one pot reaction.

In embodiments of the invention, the linking group comprises an azide and the tagging group comprises an azide reactive group. In embodiments of the invention, the linking group is, or comprises, 6-azide-glucose (6-azido-6-deoxy-D-glucose). In embodiments of the invention, the tagging group is an affinity tag. In further embodiments, the affinity tag comprises biotin and biotin derivatives. In a preferred embodiment, the biotin tag comprises PEG-dibenzocyclooctyne (DBCO)-biotin.

The step of adding the biotin tag to the linking group comprising an azide can be accomplished by contacting the 5hmC modified with an azide-containing linking group with biotin that comprises an azide-reactive group.

In embodiments, the step of enriching the affinity tagged DNA comprises affinity purification using streptavidin linked to a support when the affinity tag comprises biotin. The enriched for DNA can be amplified (i.e., the copy number increased) to create a library of DNA sequences that contained 5mC in the low input sample. Amplification of the enriched DNA can be accomplished by polymerase chain reaction using primers complimentary to the ligated adapter DNA. In preferred embodiments, the affinity tag comprises biotin and the affinity tagged DNA is enriched using streptavidin linked to a support (e.g., streptavidin-beads) and the PCR is performed directly on the enriched DNA while it is attached to the support via the biotin-streptavidin.

In one aspect, the invention provides a method for selectively sequencing 5mC containing DNA from a DNA sample comprising the steps of:
(a) adding a blocking group to the endogenous 5-hydroxymethylcytosine (5hmC) in the DNA sample;
(b) converting the 5mC in the DNA sample to 5hmC;
(c) adding a linking group to the 5hmC from step (b);
(d) ligating adapter DNA to the DNA sample;

(e) adding an affinity tag to the to the linking group from step (c);
(f) enriching for the affinity tagged DNA from step (e); and
(g) amplifying the enriched DNA from step (f); and
(h) sequencing the enriched for DNA.

In aspects, the invention involves a method for selectively sequencing 5mC containing DNA from a DNA sample comprising the steps of:
(a) adding a blocking group to the endogenous 5-hydroxymethylcytosine (5hmC) in the DNA sample;
(b) converting the 5mC in the DNA sample to 5hmC;
(c) adding an affinity tag to the 5hmC from step (b);
(d) enriching for the affinity tagged DNA; and
(e) sequencing the enriched for DNA.

In embodiments of the invention, the DNA sample contains about 1 ng to about 10 ng of DNA, about 1 ng to about 5 ng of DNA, less than 10 ng of DNA, less than about 5 ng of DNA, or less that about 2 ng of DNA. In embodiments of the invention, the DNA sample comprises circulating cell-free DNA (cfDNA).

In embodiments of the invention, the blocking group is a glucose moiety. The glucose blocking group can be added to the endogenous 5hmC by contacting the DNA sample with UDP-glucose in the presence of β-glycosyltransferase ((βGT).

In embodiments of the invention, the step of converting the 5mC in the DNA sample to 5hmC comprises contacting the DNA sample with a ten eleven translocation (TET) enzyme. In embodiments of the invention, the TET enzyme is TET1. In further embodiments, the TET1 is NgTET1. In embodiments of the invention, the TET enzyme concentration is less than 3 µM, less than 2 µM, or less than 1 µM. In embodiments, the TET1 enzyme concentration is between about 0.5 µM and about 1 µM, for example about 0.75 µM.

The sequencing method comprises the step of adding a linking group to the 5hmC generated from the endogenous 5mC, wherein the affinity tag is added to the 5hmC via the linking group. The linking group can be a modified glucose moiety, and the step of adding the linking group to the 5hmC comprises providing UDP linked to the modified glucose in the presence of βGT. In embodiments of the invention, the linking group comprises an azide and the tagging group comprises an azide-reactive group. In embodiments, the linking group is, or comprises, a 6-azide-glucose moiety.

In embodiments of the invention, the affinity tag comprises biotin or a biotin derivative. The biotin tag can be added, e.g., to the linking group by contacting the 5hmC that has been modified with the 6-azide-glucose linking group with biotin that comprises an azide-reactive group. In a preferred embodiment, the biotin tag comprises PEG-dibenzocyclooctyne (DBCO)-biotin.

In embodiments, the step of enriching the affinity tagged DNA comprises affinity purification using streptavidin linked to a support when the affinity tag comprises biotin. The enriched for DNA can be amplified (i.e., the copy number increased) to create a library of DNA sequences that contained 5mC in the low input sample. Amplification of the enriched DNA can be accomplished by polymerase chain reaction using primers complimentary to the ligated adapter DNA. In preferred embodiments, the affinity tag comprises biotin and the affinity tagged DNA is enriched using streptavidin linked to a support (e.g., streptavidin-beads) and the PCR is performed directly on the enriched DNA while it is attached to the support via the biotin-streptavidin.

In one aspect, the invention provides a kit for performing the methods disclosed herein. In embodiments, the kit comprising a TET enzyme; a β-glycosyltransferase ((βGT); a blocking group; a linking group; and a tagging group, and instructions for performing the method. In further embodiments, the TET enzyme is TET1; the blocking group is UDP-glucose; the linking group is UDP-6-azide glucose; and/or the tagging group is a DBCO-biotin or derivative thereof. In further embodiments, the TET1 is NgTET1 and the tagging group is PEG-DBCO-biotin. In embodiments, the kit further comprises adapter DNA; reagents and enzymes for repairing and optionally tailing the sample DNA; reagents and enzyme for ligating the adapter DNA to the sample DNA; reagents and materials for affinity purification; and/or reagents and enzymes for PCR amplification. In embodiments, the kit comprises reagents for isolating low-input DNA from a sample, for example cfDNA from blood, plasma, or serum.

DETAILED DESCRIPTION OF THE INVENTION

Figure 1:
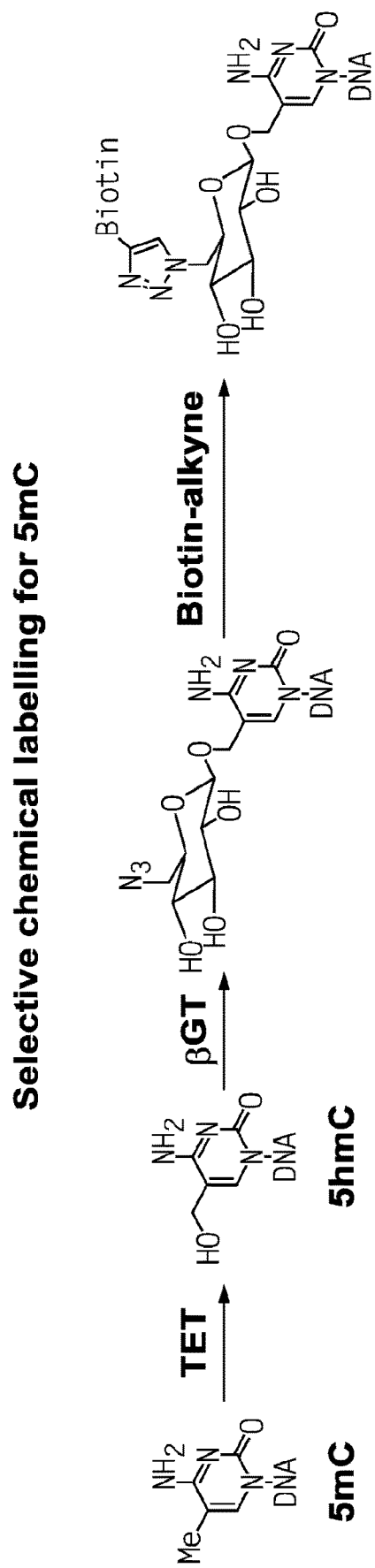
FIG. 1. Selective labeling reaction of 5mC. 5mC is converted to 5hmC by TET enzyme and then captured and labeled with an azide-modified glucose by βGT, which is then linked to a biotin group through click chemistry.

The present invention provides methods of generating a library of, and sequencing, low input DNA containing 5mC. The present invention utilizes methods for selectively tagging 5mC in a DNA sample. The selectively tagged DNA population can then be isolated and sequenced. Detecting aberrant 5mC (and 5hmC) changes in cfDNA represent attractive noninvasive approaches for cancer diagnostics; especially when they could provide tissue-of-origin information from circulating blood, which is crucial to determining the location of the tumors in early diagnostics.

DNA Samples

By combining enzymatic reactions and chemical labelling, the present invention provides a method for selective capture, enrichment, and sequencing of DNA containing 5mC from cfDNA and other low-quantity DNA samples. The methods provided herein are particularly useful on low-input DNA that cannot be readily analyzed using previous methods for sequencing 5mC-containing DNA. Low-input refers to DNA samples containing small quantities of DNA, in particular, about 10 ng DNA or less. The methods of the present invention can be performed on a DNA sample comprising 5mC where the DNA sample comprises about 1 to about 10 ng of DNA, about 2 to about 5 ng of DNA, less than 5 ng, and less than 2 ng of DNA.

Circulating cell-free DNA (cell-free DNA or cfDNA) is DNA found in the blood (i.e., not present within a cell). cfDNA can be isolated from blood or plasma using methods known in the art. Commercial kits are available for isolation of cfDNA including, for example, the Circulating Nucleic Acid Kit (Qiagen).

5hmC Blocking Group

In the methods of the present invention, endogenous 5hmC moieties in the sample DNA are rendered non-reactive to the subsequent steps by adding a blocking group to the endogenous 5hmC. In one embodiment, the blocking group is glucose. The glucose blocking group is added to the hydroxymethyl group of 5hmC by contacting the DNA sample with uridine diphosphate (UDP)-glucose in the presence of a β-glycosyltransferase ((βGT). βGT is an enzyme that catalyzes a chemical reaction in which a beta-D-glucosyl (glucose) residue is transferred from UDP-glucose to a 5-hydroxymethylcytosine residue in a nucleic acid.

Converting 5mC to 5hmC

Once the endogenous 5hmC groups in the DNA sample are blocked, the 5mC groups in the DNA sample are converted to 5hmC. The 5mC groups in the DNA sample are converted to 5hmC using a ten eleven translocation (TET) enzyme, for example TET1. The TET enzymes (TET1, 2, and 3) are a family of enzymes that catalyze the transfer of an oxygen molecule to the N5 methyl group on the modified cytosine ring resulting in the formation of 5-hydroxymethylcytosine (5hmC). TET enzymes that can be used to convert 5mC to 5hmC, therefore include TET1, TET2, and/or TET3 enzymes, and further include engineered mutants and natural variants thereof. In embodiments, the TET enzyme is from the protist *Naegleria gruberi* (NgTET). In embodiments of the invention, the concentration of the TET1 enzyme in the conversion reaction is less than 3 µM, less than 2 µM, or less than 1 µM. In embodiments, the concentration of TET1 enzyme in the conversion reaction is between 0.5 µM and 1 µM.

Linking Groups and Tagging Groups

In embodiments of the invention, the 5mC in a DNA sample is tagged (labelled) by attaching a tagging group to the 5hmC following conversion of the 5mC to 5hmC. A tagging group is a moiety that provides a functional ability when bound to the sample DNA, for example, identification, isolation, and/or purification of the tagged sample DNA. In embodiments of the present invention, a tagging group is added in order to, for example, facilitate enrichment of the DNA comprising 5hmC (converted from 5mC). In one embodiment, the tag is biotin (including derivatives of biotin). In embodiments of the invention, the biotin tag comprises dibenzocyclooctyne (DBCO)-biotin or derivatives thereof, for example, polyethylene glycol (PEG)-DBCO-biotin.

In embodiments of the invention, the tagging group is attached to the 5hmC via a linking group. The linking group can be a glucose moiety modified or functionalized for use in click chemistry or other coupling chemistries known in the art. The modified glucose linking group can be added to the 5hmC by contacting the 5hmC with UDP linked to the modified glucose in the presence of βGT as described above for adding a blocking group to the endogenous 5hmC. In embodiments, the concentration of βGT in the reaction adding a modified glucose moiety to 5hmC is less than about 2 µM, less than about 1 µM, less than 0.5 µM, less than about 0.3 µM. In embodiments, the concentration of βGT in the reaction adding a modified glucose moiety to 5hmC is between about 0.1 µM to about 1 µM or between about 0.2 µM and about 0.5 µM. In a preferred embodiment, the concentration of βGT in the reaction adding a modified glucose moiety to 5hmC is about 0.3 µM. In embodiments of the invention, the conversion of 5mC to 5hmC by TET and the addition of a modified glucose to the 5hmC is performed as a one pot reaction (i.e., the reaction is performed in a single reaction vessel).

In embodiments of the invention, the tagging group is attached to the converted 5hmC via a linking group utilizing click chemistry (for example, azide-alkyne cycloaddition). For example UDP-6-azide glucose (6-azido-6-deoxy-D-glucose linked to UDP) and βGT are used to attach to 5hmC a glucose moiety modified with an azide group. Biotin (or other tag) comprising an azide-reactive group can then be reacted with the azide group. Azide reactive groups utilized in click chemistry are known in the art and include, for example, alkyne and cyclooctyne derivatives such as dibenzocyclooctyne (DIBO) and azadibenzocyclooctyne (ADIBO or DBCO).

Ligation of DNA Adapters

A DNA adapter or DNA linker is a short, chemically-synthesized, single- or double-stranded oligonucleotide that can be ligated to one or both ends of other DNA (or RNA) molecules. Double-stranded adapters can be synthesized so that each end of the adapter has a blunt end or a 5' or 3' overhang (i.e., sticky ends). DNA adapters are ligated to the sample DNA to provide sequences for PCR amplification with complimentary primers and for cloning and/or library creation.

Prior to ligation of the adapters to the sample DNA, the ends of the sample DNA are typically prepared for ligation by, for example, end repair, creating blunt ends with 5' phosphate groups. The blunt ends can be used for ligation to adapters or overhangs can be created prior to ligation by, e.g., a tailing reaction. Tailing is an enzymatic method for adding a non-templated nucleotide to the 3' end of a blunt, double-stranded DNA molecule. A-tailing of the 3' ends (i.e., adding a dA to the 3' ends) can be used to facilitate ligation to adapters with complementary dT-overhangs.

In the present methods, ligation of adapters can be performed on the unmodified DNA sample; after the step of adding a blocking group to the endogenous 5hmC (and before converting the 5mC to 5hmC; or after adding a linking group to the 5hmC or adding a tag to the linking group. In a preferred embodiment, the adapters are ligated to the sample DNA prior to affinity purification, so that the enriched for DNA (i.e., the DNA containing 5mC in the original sample) can be amplified directly from the support used for affinity purification (e.g., streptavidin beads).

Enrichment of Tagged DNA

After the sample DNA is tagged, the tag can be used to purify the tagged DNA (i.e., the sample DNA originally containing 5mC). The enrichment method will depend upon the tagging group employed. The use of a biotin tag allows for affinity purification utilizing streptavidin linked to a support (for example streptavidin beads) by methods known in the art.

Creation of a Next Generation Sequencing Library

Once the tagged DNA is enriched, it is PCR-amplified to generate a library of 5mC-containing DNA for next generation sequencing. The primers for PCR have sequences corresponding (complimentary) to double-stranded adapter DNA that has been previously ligated to the sample DNA. In embodiments of the invention, the tagged DNA is amplified by PCR directly from the support used to enrich the tagged DNA (e.g., while the enriched affinity tagged DNA is linked to the streptavidin-beads).

The methods provided herein, including the reagents, the steps and their order, enable the generation of libraries of 5mC-containing DNA from low input samples including circulating cell-free DNA. These libraries can be sequence using high-throughput next generation sequencing methods.

Kits

Aspects of the invention also provide a kit for performing the methods described herein. Kits may comprise instructions for performing the method described herein and one or more containers comprising the enzymes and reagents discussed herein and/or utilized in the Examples. Kits, for example, may comprise a TET enzyme; a β-glycosyltransferase ((βGT); a blocking group (e.g., UDP)-glucose); a linking group (e.g., UDP-6-azide glucose); and a tagging group (e.g., a DBCO-biotin or derivative thereof). Preferably the TET enzyme is TET1, in particular NgTET1. Preferably, the tagging group is PEG-DBCO-biotin.

The kits may additionally comprise adapter DNA; reagents and enzymes for repairing and optionally tailing the sample DNA; reagents and enzyme for ligating the adapter DNA to the sample DNA; reagents and materials for affinity purification (e.g., streptavidin beads); and/or reagents and enzymes for PCR amplification.

EXAMPLES

Methods

Spike-in Amplicon Preparation.

The C, 5mC and 5hmC spike-in controls (FIGS. 3a and 3b) were generated as previously described (Song et al., 2017, Cell Res., doi:10.1038/cr.2017.106, incorporated herein by reference). To generate 1 CpG, 2 CpG, 5 CpG, 10 CpG and 20 CpG methylated spiked-in controls (FIG. 3b), lambda DNA (Thermo Fisher) was PCR amplified by Taq DNA Polymerase (New England Biolabs) and purified by AMPure XP beads (Beckman Coulter) in nonoverlapping ~180 bp amplicons. Primers sequences were as follows: 1 CpG FW-TTGGCCATACTACTAAATCCTG, RV-GGT-CAAAAAGAAGAAGTAAGCAC; 2 CpG FW-AGCTT-CAAGCCAGAGTTGTC, RV-AGAACAACCTGACCCAGC; 5 CpG FW-CCTGAT-GAAACAAGCATGTC, RV-CATTACTCACTTCCC-CACTT; 10 CpG FW-CAATGCCACAAAGAAGAGTC, RV-CCTCTTTTCATCTCACTACC; 20 CpG FW-GAGGT-TATCCGTTCCCGTGG, RV-TCGTCACGCATGTTCTGC. 100 ng of each amplicon was then methylated in 20 μl solution containing 1× NEBuffer 2, 0.64 mM 5-adenosyl-methionine and 20 U M.SssI CpG Methyltransferase (New England Biolabs) for 2 hr at 37° C., followed by 20 min heat inactivation at 65° C. The methylated amplicons were purified by AMPure XP beads.

Cell-Free 5mC Labeling, Library Construction, Capture and High-Throughput Sequencing.

cfDNA (1-5 ng) was incubated in 30 μl solution containing 50 mM HEPES buffer (pH 8), 25 mM $MgCl_2$, 200 μM UDP-Glc (New England Biolabs), and 15 U βGT (Thermo Fisher) for 1 hr at 37° C. to block endogenous 5hmC. Following the incubation, the cfDNA was purified with AMPure XP beads (Beckman Coulter).

Next, 5mC was converted to 5hmC, which was linked to an azide-modified glucose by incubating the cfDNA in 30 μl solution containing 50 mM HEPES buffer (pH 6.9), 10 mM $MgCl_2$, 75 mM ammonium iron (II) sulfate, 2 mM ascorbic acid, 1 mM α-ketoglutarate, 150 μM UDP-6-N3-Glc (Active Motif), 1 mM dithiothreitol, 0.3 μM βGT (15 U), and 0.5 μM TET1 for 1 hr at 37° C. After that, 0.4 U of Proteinase K (New England Biolabs) was added to the reaction mixture and incubated for 30 min at 37° C. Following the incubation, the cfDNA was purified with AMPure XP beads. Subsequently, the cfDNA was end-repaired, 3'-adenylated and ligated to KAPA Single-Indexed Adapter using KAPA Hyper Prep Kit (Kapa Biosystems) according to the manufacturer's instructions.

Ligated DNA was incubated in a 20 μl solution containing 50 mM HEPES buffer (pH 8), 25 mM $MgCl_2$, and 1 mM DBCO-PEG4-biotin (Click Chemistry Tools) for 2 hr at 37° C. Next, 10 μg sheared salmon sperm DNA (Thermo Fisher) was added to the reaction mixture and the DNA was purified by Micro Bio-Spin 30 Column (Bio-Rad).

The purified DNA was incubated with 0.5 μL M270 streptavidin beads (Thermo Fisher) that were pre-blocked with salmon sperm DNA in buffer 1 (5 mM Tris pH 7.5, 0.5 mM EDTA, 1 M NaCl and 0.2% Tween 20) for 30 min. The beads were subsequently washed three times with each of buffer 1, buffer 2 (buffer 1 without NaCl), buffer 3 (buffer 1 with pH 9) and buffer 4 (buffer 3 without NaCl). All binding and washing were done at room temperature with gentle rotation.

Beads were then resuspended in water and the DNA amplified with 14 cycles of PCR amplification using KAPA HiFi HotStart ReadyMix (Kapa Biosystems). The PCR products were purified using AMPure XP beads. Pair-end 75 bp sequencing was performed on an Illumina instrument.

Results and Discussion

By combining enzymatic reactions and chemical labelling, an enrichment method was developed that allows for selective capture and sequencing of 5mC in cfDNA and in other low-input DNA samples. This selectivity allows the decoupling of the antagonistic 5mC and 5hmC signals from the cfDNA. This method was applied to clinical samples and produced successful next generation sequencing (NGS) libraries, even from less than 2 ng of cfDNA. The specificity of 5mC enrichment was confirmed and it was demonstrated that cell-free 5mC represents distinct epigenetic features from cell-free 5hmC.

Figure 2:
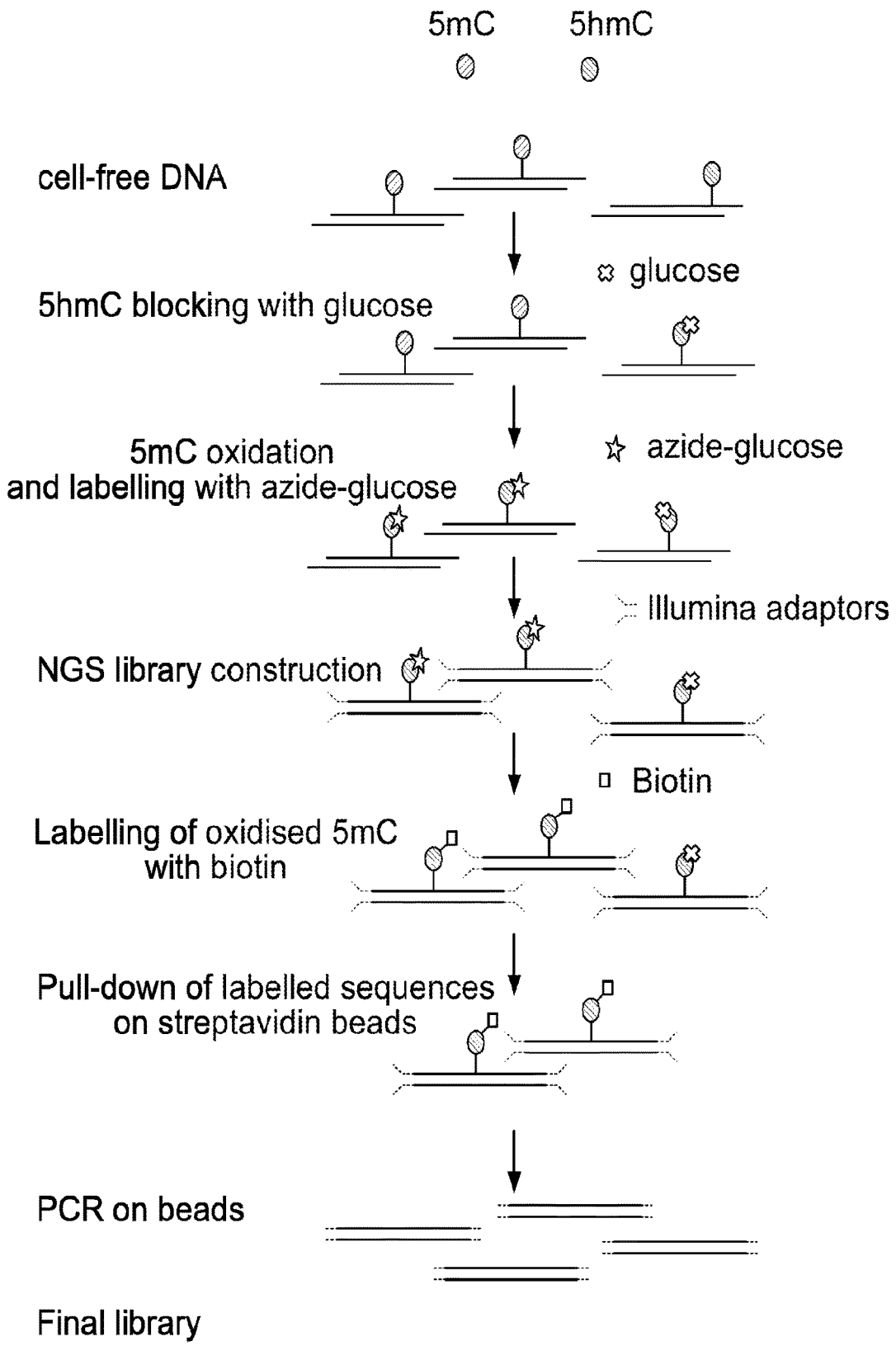
FIG. 2. The general procedure of cell-free 5mC sequencing. Endogenous 5hmC in cfDNA sample is blocked. Then 5mC is converted to 5hmC and labeled with azide-modified glucose by TET and PGT. The cfDNA is ligated with Illumina adapters and tagged with biotin on 5hmC for pull-down with streptavidin beads. The final library is completed by direct PCR from streptavidin beads.

The methods of the present invention render the endogenous 5hmC in a cfDNA sample inactive and then oxidizes 5mC in the cfDNA to 5hmC in order to selectively label it (FIG. 1). Specifically, the endogenous 5hmC in cfDNA was blocked with a normal glucose using β-glucosyltransferase (βGT) so that the endogenous 5hmC was no longer reactive. Next, TET and βGT were used in a one-pot reaction to label the 5mC in cfDNA with an azide-modified glucose (by converting the 5mC to 5hmC and attaching the azide-modified glucose to the 5hmC). The labeled cfDNA was then ligated with sequencing adapters and then subsequently tagged with a biotin group by click chemistry. Finally, the 5mC-containing cfDNA was captured on streptavidin beads amplified by PCR directly from the beads to create the final library for sequencing (FIG. 2).

Figure 3A:
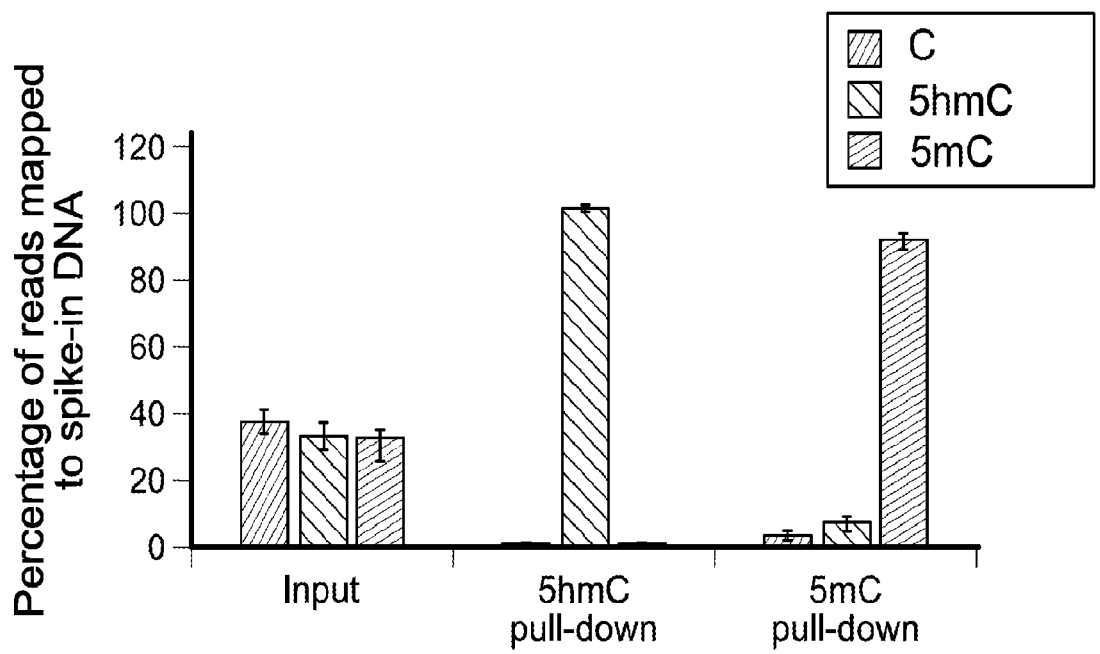
FIG. 3a. Spike-in DNA enrichment comparison between cell-free 5mC and 5hmC sequencing. Percentage of reads mapped to spike-in amplicons containing C, 5mC or 5hmC in the final input cfDNA (unenriched) or 5mC enriched cfDNA sequencing libraries.
Figure 3B:
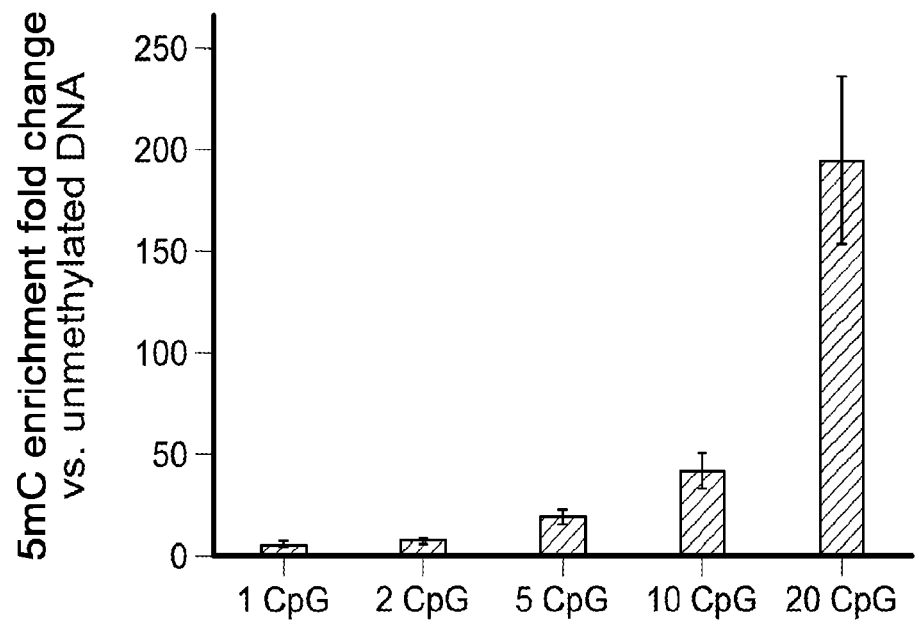
FIG. 3b. Spike-in controls show cell-free 5mC sequencing preferentially enriched high-density CpG methylated DNA. Fold enrichment of various spike-in amplicons carrying increasing numbers of methylated CpG, compared to an unmethylated control DNA in the cell-free 5mC sequencing libraries.

Using spike-in DNA controls, it was demonstrated that the method of the present invention specifically enriched for 5mC-containing DNA over cytosine (C) or 5hmC-containing DNA (FIG. 3a). The method preferentially enriched highly CpG methylated DNA (FIG. 3b).

The enrichment-based 5mC selective chemical labeling method of the present invention has several advantages. First, unlike bisulfite sequencing, it does not degrade cfDNA. By the methods of the present invention, 1-5 ng cfDNA can be readily sequenced for cell-free 5mC, requiring much less cfDNA and retrieving more information than bisulfite sequencing. Second, the enrichment for 5mC allows cost-effective sequencing and amplifies the low-frequency 5mC signals from tissue-specific contributions of cfDNA. Third, the use of robust and specific biotin/streptavidin interaction for enrichment is preferred over traditional antibody/antigen interaction in this low-input application where maximizing the signal-to-noise ratio is desirable. Fourth, the bias toward high-density CpG sites allows enrichment of the most informative 5mC regions in the genome, namely the CpG islands, further reducing the sequencing cost and background noises.

Figure 4:
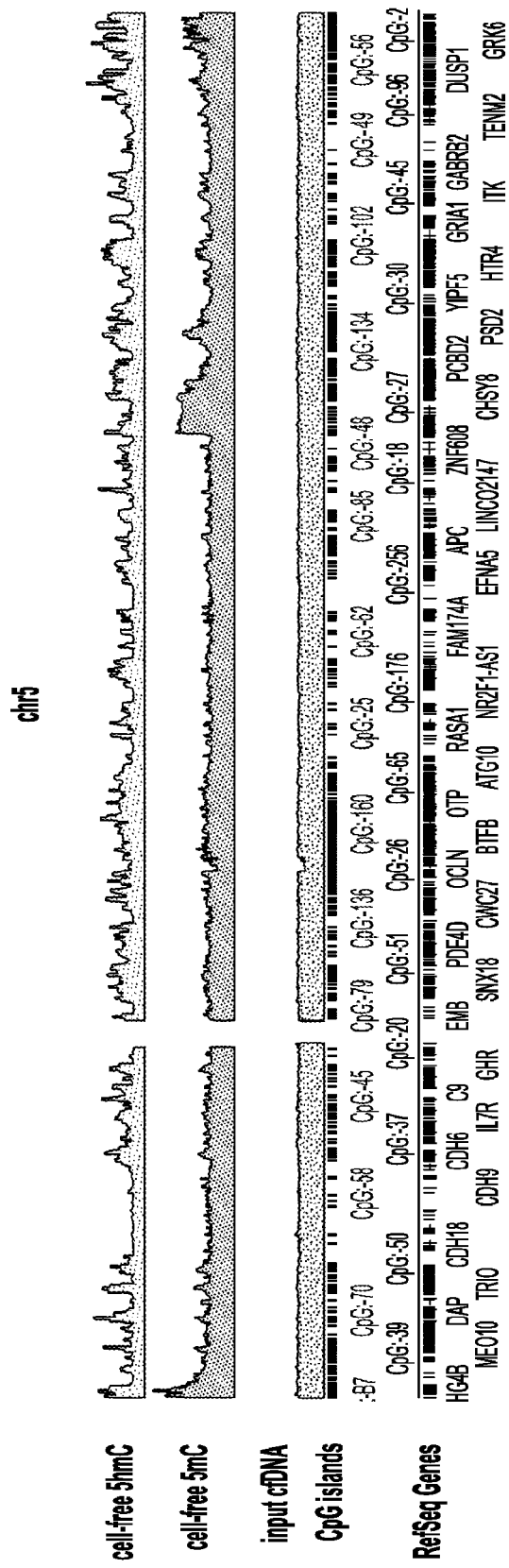
FIG. 4. Genome browser view of the 5mC distribution compared to cell-free 5hmC distribution and the unenriched input cfDNA in chromosome 5. Cell-free hydroxymethylome and methylome showed different patterns. While cell-free 5hmC tends to be enriched at gene-rich regions, cell-free 5mC is mostly enriched at CpG islands.
Figure 5A:
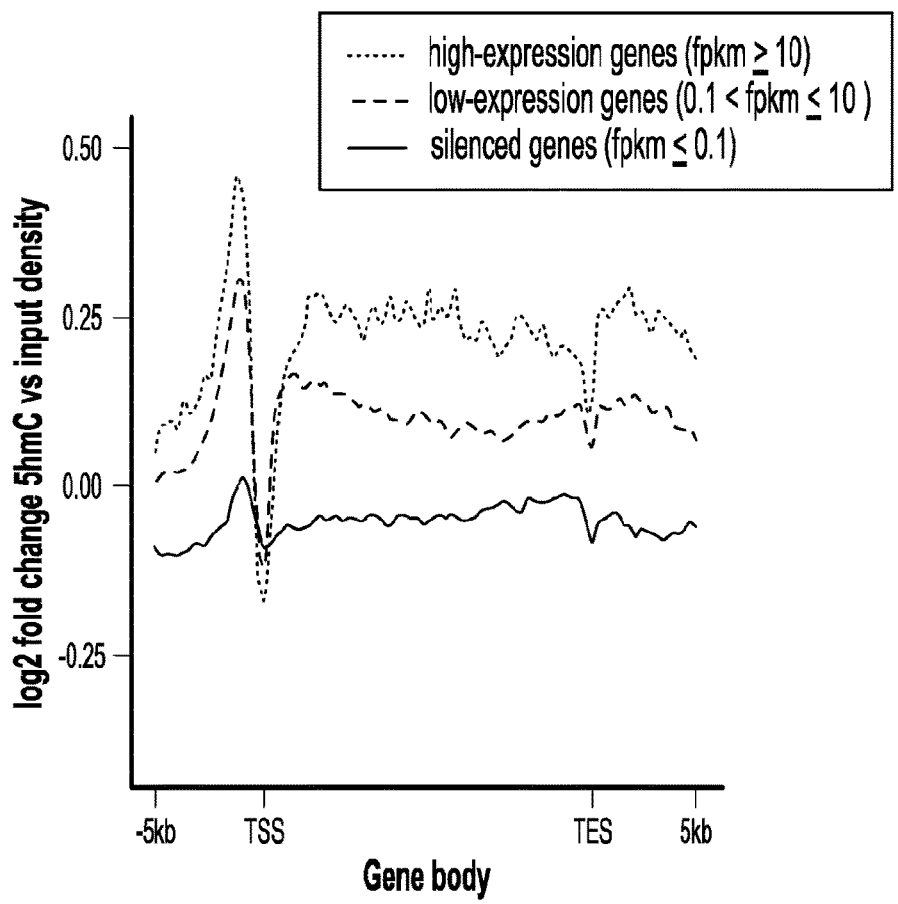
FIG. 5a. Metagene profiles of cell-free 5hmC signals in genes ranked according to their expression in cell-free RNA-Seq. Cell-free 5hmC is positively correlated with cell-free RNA expression.
Figure 5B:
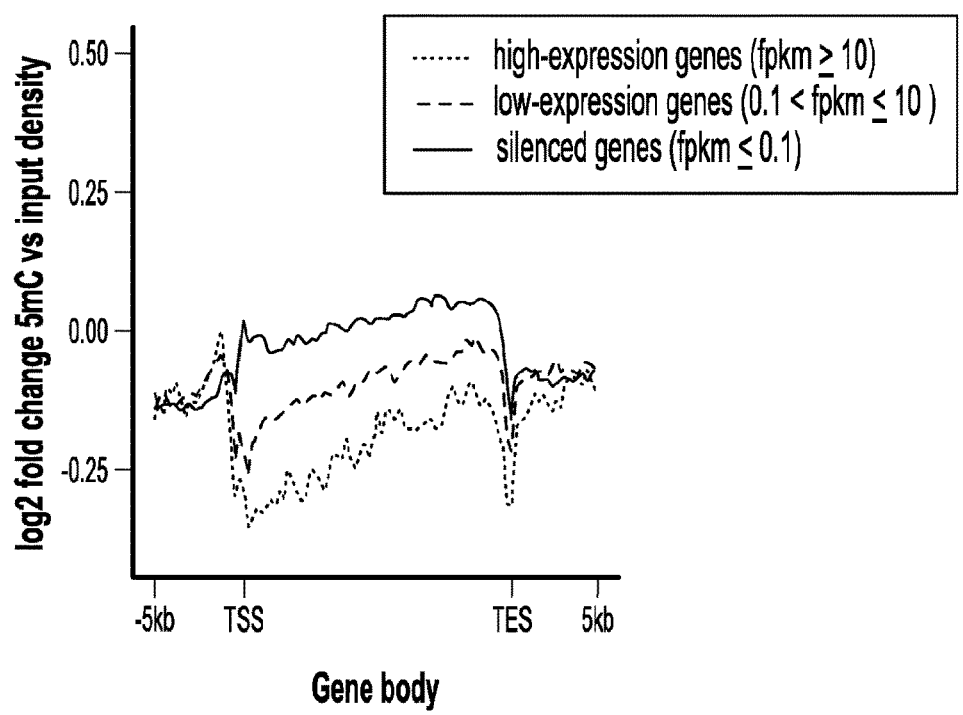
FIG. 5b. Metagene profiles of cell-free 5mC signals in genes ranked according to their expression in cell-free RNA-Seq. Cell-free 5mC is negatively correlated with cell-free RNA expression.
Figure 6:
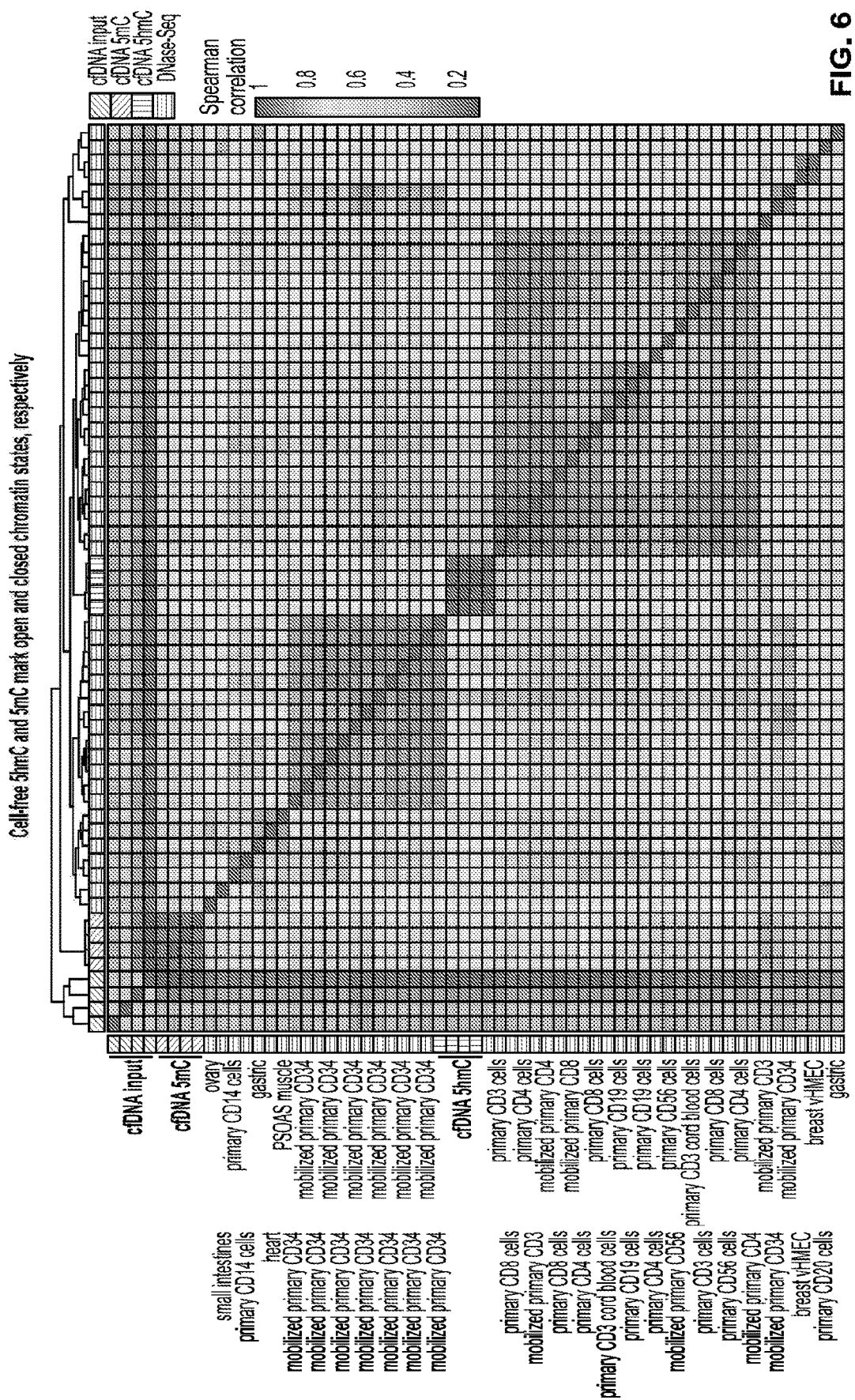
FIG. 6. Cell-free 5hmC and 5mC mark open and closed chromatin states, respectively. Cell-free 5hmC and cell-free 5mC were compared using chromatin state data from a publicly-available database.

Cell-free 5mC and 5hmC from healthy individuals was sequenced and demonstrated distinct genomic distributions, while cell-free 5hmC tends to enrich at gene-rich region, cell-free 5mC is enriched at CpG islands (FIG. 4). As previously demonstrated, cell-free 5hmC correlated with cell-free RNA expression (FIG. 5a). See also Song et al. Cell Research (2017):1-12 (FIG. 1C of Song et al. and associated methods, incorporated herein by reference). The same analysis was performed on cell-free 5mC and it showed the exact opposite trend and anticorrelated with cell-free RNA expression (FIG. 5b). These results demonstrated that by performing the cell-free 5mC sequencing methods of the present invention, additional information was extracted from cfDNA that corresponds to the repressive and closed chromatin state.

Figure 7A:
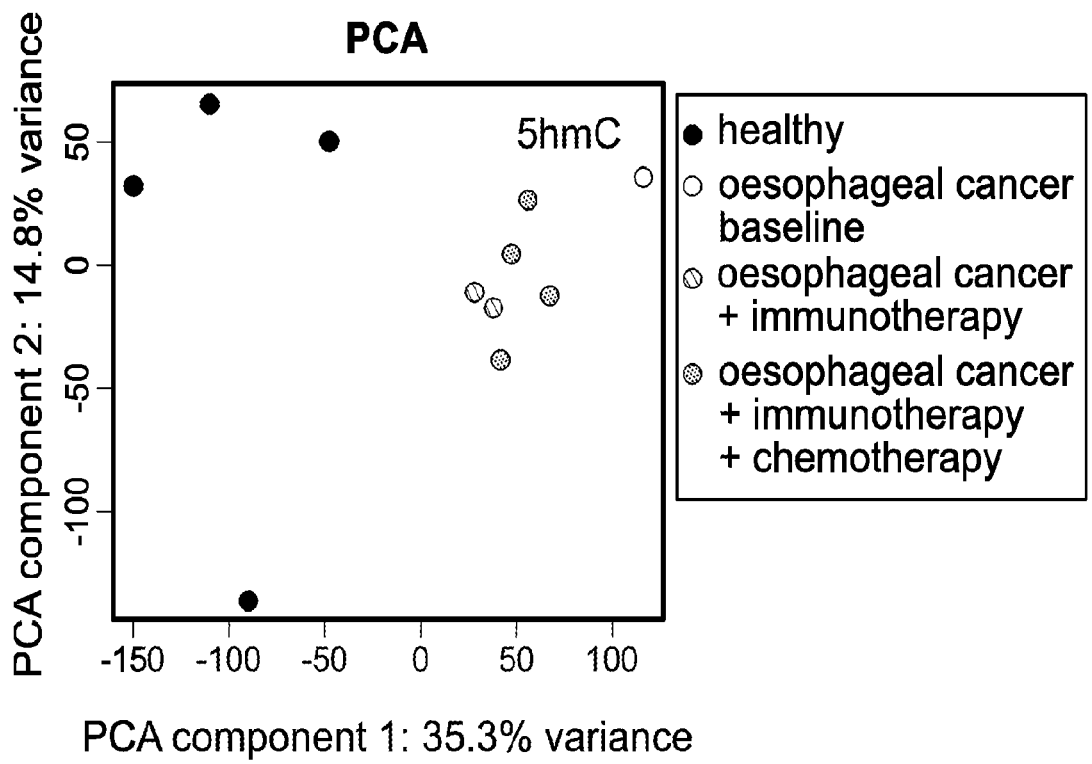
FIG. 7a. Principal component analysis (PCA) plot of 5hmC signals from healthy individuals and oesophageal cancer patients.
Figure 7B:
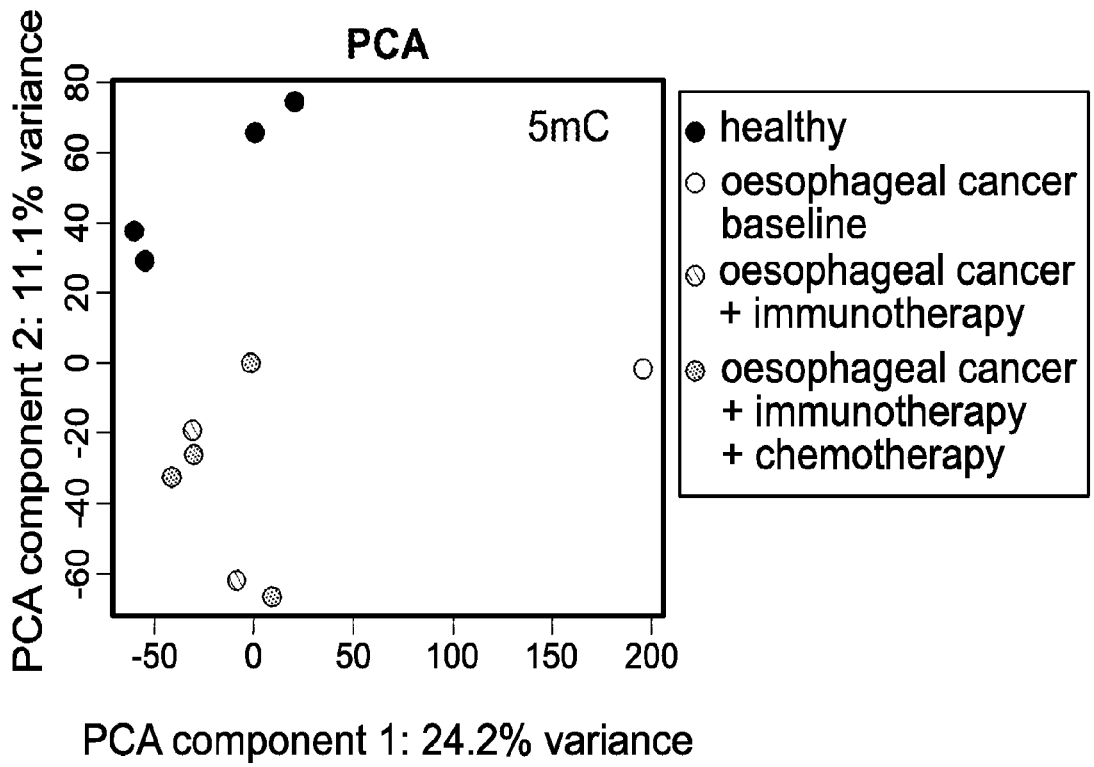
FIG. 7b. PCA plot of 5mC signals from healthy individuals and oesophageal cancer patients.
Figure 7C:
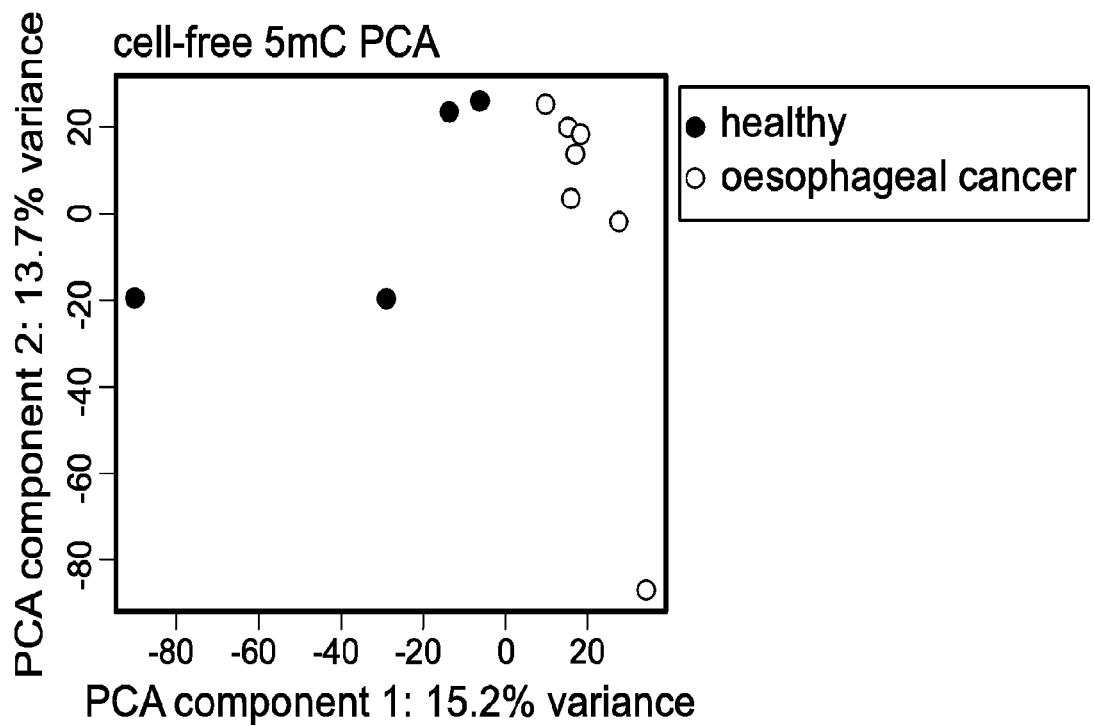
FIG. 7c. PCA plot of CpG island 5mC signals in cfDNA from healthy individuals and oesophageal cancer patients.
Figure 7D:
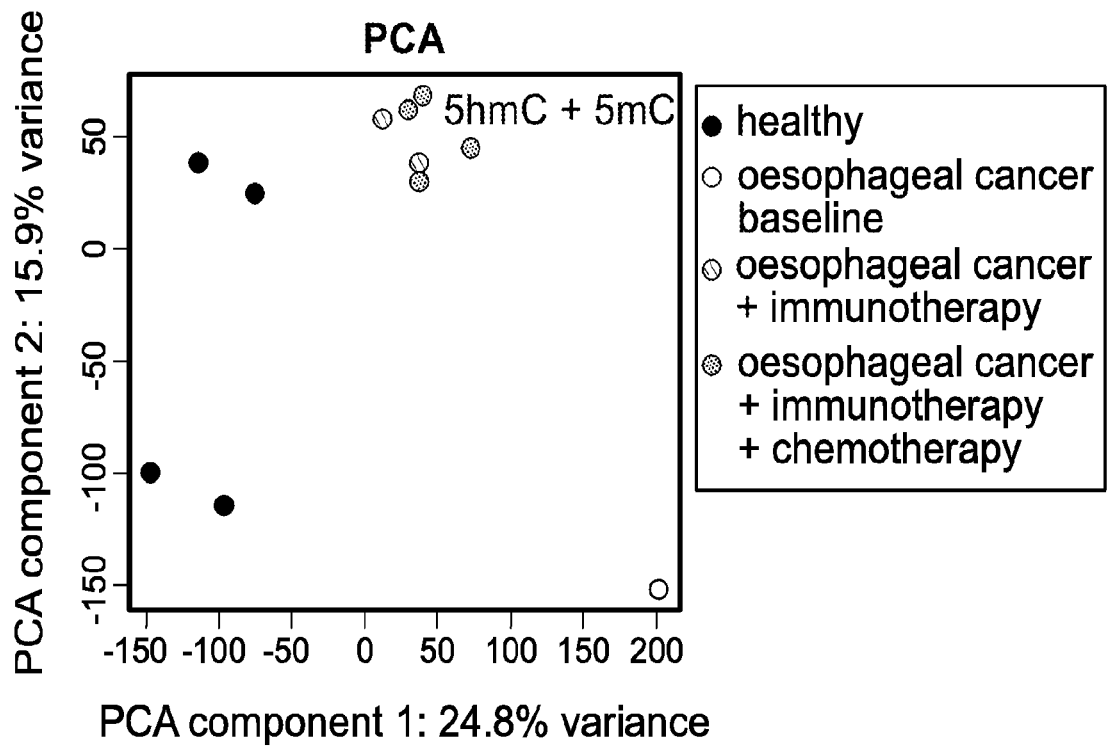
FIG. 7d. PCA plot of 5mC and 5hmC signals from healthy individuals and oesophageal cancer patients.

As a proof of concept, the cell-free 5mC sequencing method was applied to cfDNA from oesophageal cancer patients and showed that the cell-free 5mC signal readily separated oesophageal cancer from the healthy controls (FIG. 7b, FIG. 7c). The combination of 5hmC signal and 5mC signal improved the separation of oesophageal treatment stages (FIG. 7d). These results demonstrate the potential of cell-free 5mC for cancer detection. Genome-wide maps of 5mC in cfDNA from healthy subjects and cancer patients demonstrate the unique features of cell-free 5mC distribution and the utility of mapping cell-free 5mC for cancer detection. The methods of the present invention, together with cell-free 5hmC sequencing, have applications in other diagnostic areas, including measurement of tissues health and death in neurodegenerative disease, cardiovascular disease, diabetes and others. It can also be used to track fetal development in pregnancy via the analysis of maternal blood and to test for various prenatal or congenital issues.

The invention claimed is:

1. A method for creating a library of 5-methylcytosine (5mC) containing DNA from a low-input DNA sample comprising the steps in order of:
   (a) obtaining a low-input DNA sample;
   (b) adding a blocking group to the endogenous 5-hydroxymethylcytosine (5hmC) in the DNA sample;
   (c) converting the 5mC in the DNA sample to 5hmC with *Naeglerai gruberi* TET1 (NgTET1);
   (d) adding a linking group to the 5hmC from step (c);
   (e) after step (d), ligating DNA adapters to the DNA sample;
   (f) after step (e), adding an affinity tag to the linking group from step (d);
   (g) enriching for the affinity tagged DNA from step (f) by affinity purification utilizing a support; and
   (h) amplifying the enriched DNA from step (g), wherein amplifying the enriched DNA comprises PCR directly on the enriched DNA linked to the support.

2. The method of claim 1, wherein the DNA sample comprises less than about 10 ng or less than about 5 ng of DNA.

3. The method of claim 1, wherein the DNA sample comprises circulating cell-free DNA (cfDNA).

4. The method according to claim 1, wherein the linking group is a modified glucose moiety and the step of adding a linking group to the 5hmC from step (c) comprises providing UDP linked to the modified glucose moiety in the presence of βGT.

5. The method of claim 4, wherein the modified glucose moiety is a 6-azide-glucose moiety.

6. The method according to claim 1, wherein the affinity tag comprises biotin and the affinity purification utilizes streptavidin linked to a support.

7. The method of claim 6, wherein the step of adding the biotin affinity tag to the linking group comprises contacting the 5hmC modified with a linking group with biotin that comprises an azide-reactive group.

8. The method of claim 6 wherein the biotin comprises PEG-dibenzocyclooctyne (DBCO)-biotin.

9. The method according to claim 6, wherein amplifying the enriched DNA comprises PCR directly on the enriched DNA linked to the support by the biotin-streptavidin.

10. The method of claim 1, wherein the blocking group is glucose.

11. The method of claim 8, wherein the glucose blocking group is added to the endogenous 5hmC by contacting the DNA sample with UDP-glucose in the presence of β-glycosyltransferase (βGT).

12. The method according to claim 1, wherein steps (c) and (d) are performed as a one pot reaction.

13. A method for selectively sequencing 5mC containing DNA from a DNA sample comprising the steps in order of:
   (a) adding a blocking group to the endogenous 5-hydroxymethylcytosine (5hmC) in the DNA sample;
   (b) converting the 5mC in the DNA sample to 5hmC with *Naegleria gruberi* TET1 (NgTET1);
   (c) adding a linking group to the 5hmC from step (b);
   (d) after step (c), ligating adapter DNA to the DNA sample;
   (e) after step (d), adding an affinity tag to the to the linking group from step (c);
   (f) enriching for the affinity tagged DNA from step (e) by affinity purification utilizing a support;
   (g) amplifying the enriched DNA from step (f), wherein amplifying the enriched DNA comprises PCR directly on the enriched DNA linked to the support; and
   (h) sequencing the amplified DNA.

14. The method of claim 13, wherein the DNA sample comprises less than about 10 ng or less than about 5 ng of DNA.

15. The method of claim 13, wherein the DNA sample comprises circulating cell-free DNA (cfDNA).

16. The method according to claim 13, wherein the linking group is a modified glucose moiety and the step of adding a linking group to the 5hmC from step (b) comprises providing UDP linked to the modified glucose in the presence of βGT.

17. The method of claim 16, wherein the modified glucose moiety is a 6-azide-glucose moiety.

18. The method according to claim 13, wherein the affinity tag comprises biotin and the affinity purification utilizes streptavidin linked to a support.

19. The method of claim 18, wherein the step of adding the biotin tag to the linking group comprises contacting the 5hmC modified with a linking group with biotin that comprises an azide-reactive group.

20. The method of claim 18 wherein the biotin comprises PEG-dibenzocyclooctyne (DBCO)-biotin.

21. The method according to claim 18, wherein amplifying the enriched DNA comprises PCR directly on the enriched DNA linked to the support by the biotin-streptavidin.

22. The method of claim 13, wherein the blocking group is glucose.

23. The method of claim 22, wherein the glucose blocking group is added to the endogenous 5hmC by contacting the DNA sample with UDP-glucose in the presence of β-glycosyltransferase (βGT).

24. The method according to claim 14, wherein the concentration of the TET1 enzyme is less than 3 less than 2 or less than 1 μM.

25. The method according to claim 4, wherein the concentration of βGT is less than about 2 μM, less than about 1 μM, less than 0.5 μM, less than about 0.3 μM, between about 0.1 μM to about 1 μM, between about 0.2 μM and about 0.5 μM, or about 0.3 μM.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ttggccatac tactaaatcc tg                                              22

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
ggtcaaaaag aagaagtaag cac                                             23

<210> SEQ ID NO 3
<211> LENGTH: 20
<212> TYPE: DNA
<213> ORGANISM: Artificial Sequence
<220> FEATURE:

```
<223> OTHER INFORMATION: Primer

<400> SEQUENCE: 3
agcttcaagc cagagttgtc                                                   20

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
agaacaacct gacccagc                                                     18

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cctgatgaaa caagcatgtc                                                   20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cattactcac ttccccactt                                                   20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
caatgccaca aagaagagtc                                                   20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cctcttttca tctcactacc                                                   20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gaggttatcc gttcccgtgg                                                   20
```

```
<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
tcgtcacgca tgttctgc                                                    18
```